US009693878B2

(12) United States Patent
Kunz et al.

(10) Patent No.: US 9,693,878 B2
(45) Date of Patent: Jul. 4, 2017

(54) PATIENT-SPECIFIC GUIDE FOR ACETABULAR CUP PLACEMENT

(75) Inventors: Manuela Kunz, Kingston (CA); John F. Rudan, Kingston (CA)

(73) Assignee: Queen's University at Kingston, Kingston (CA)

( * ) Notice: Subject to any disclaimer, the term of this patent is extended or adjusted under 35 U.S.C. 154(b) by 463 days.

(21) Appl. No.: 13/510,342

(22) PCT Filed: Nov. 17, 2010

(86) PCT No.: PCT/CA2010/001828
§ 371 (c)(1),
(2), (4) Date: Jun. 7, 2012

(87) PCT Pub. No.: WO2011/060536
PCT Pub. Date: May 26, 2011

(65) Prior Publication Data
US 2012/0245647 A1    Sep. 27, 2012

Related U.S. Application Data

(60) Provisional application No. 61/262,073, filed on Nov. 17, 2009.

(51) Int. Cl.
*A61F 2/46* (2006.01)
*A61B 17/17* (2006.01)
(Continued)

(52) U.S. Cl.
CPC ........ *A61F 2/4609* (2013.01); *A61B 17/1746* (2013.01); *A61B 2017/568* (2013.01);
(Continued)

(58) Field of Classification Search
CPC ............... A61F 2/4609; A61B 17/1746; A61B 2017/568
(Continued)

(56) References Cited

U.S. PATENT DOCUMENTS 5,098,383 A    3/1992  Hemmy et al.
5,250,050 A    10/1993 Poggie et al.
(Continued)

FOREIGN PATENT DOCUMENTS

EP    1486900 A1    12/2004
WO    9325157 A1    12/1993
(Continued)

OTHER PUBLICATIONS

Office Action and Search Report for corresponding Chinese Patent Application No. 201080061145.2 dated Jun. 25, 2014.
(Continued)

*Primary Examiner* — Matthew Lawson
(74) *Attorney, Agent, or Firm* — Stephen J. Scribner

(57) ABSTRACT

Provided is a preoperatively designed guidance tool for intraoperative use during acetabular cup replacement surgery, comprising: a patient-specific template having at least one surface that registers with a selected surface of the patient's acetabulum; and a guide portion that provides an orientation or a position and orientation of an acetabular cup according to a preoperatively planned orientation or position and orientation. The guidance tool may further comprise a verification tool that cooperates with the guide portion and includes at least one mating surface that registers with a selected surface of the patient's anatomy, wherein correct positioning of the verification tool on the patient's anatomy confirms correct orientation of the patient-specific template in the patient's acetabulum. Also described herein are methods of acetabulum cup replacement surgery, and methods for transferring a preoperatively planned orientation or position and orientation of an acetabular cup to a patient during acetabulum cup replacement surgery.

13 Claims, 16 Drawing Sheets

(51) Int. Cl.
  *A61B 17/56* (2006.01)
  *A61F 2/30* (2006.01)
  *A61B 34/10* (2016.01)

(52) U.S. Cl.
  CPC ..... *A61B 2034/108* (2016.02); *A61F 2/30942* (2013.01); *A61F 2002/4687* (2013.01)

(58) Field of Classification Search
  USPC .......................... 606/81, 91, 87, 96–98, 130
  See application file for complete search history.

(56) References Cited

U.S. PATENT DOCUMENTS

| | | | |
|---|---|---|---|
| 5,682,886 A | 11/1997 | Delp et al. | |
| 5,768,134 A | 6/1998 | Swaelens et al. | |
| 5,871,018 A | 2/1999 | Delp et al. | |
| 5,910,143 A | 6/1999 | Cripe et al. | |
| 5,967,777 A | 10/1999 | Klein et al. | |
| 6,117,143 A | 9/2000 | Hynes et al. | |
| 6,214,014 B1* | 4/2001 | McGann | A61F 2/4657 606/102 |
| 6,264,698 B1* | 7/2001 | Lawes | A61B 17/7098 606/91 |
| 6,298,262 B1 | 10/2001 | Franck et al. | |
| 6,327,491 B1 | 12/2001 | Franklin et al. | |
| 6,395,005 B1* | 5/2002 | Lovell | A61B 17/1666 606/91 |
| 6,738,657 B1 | 5/2004 | Franklin et al. | |
| 6,944,518 B2 | 9/2005 | Roose | |
| 7,559,931 B2* | 7/2009 | Stone | A61B 17/175 600/424 |
| 7,651,506 B2 | 1/2010 | Bova et al. | |
| 8,043,297 B2 | 10/2011 | Grady et al. | |
| 8,092,465 B2 | 1/2012 | Metzger et al. | |
| 8,133,234 B2 | 3/2012 | Meridew et al. | |
| 8,568,487 B2 | 10/2013 | Witt et al. | |
| 8,608,749 B2 | 12/2013 | Meridew et al. | |
| 8,932,299 B2* | 1/2015 | Bono | A61B 17/1746 606/91 |
| 8,986,309 B1* | 3/2015 | Murphy | A61B 17/1746 606/87 |
| 9,138,258 B2* | 9/2015 | Geebelen | A61B 17/1631 |
| 9,211,128 B2* | 12/2015 | Gillman | A61F 2/34 |
| 2002/0077540 A1* | 6/2002 | Kienzle, III | 600/424 |
| 2004/0092932 A1 | 5/2004 | Aubin et al. | |
| 2005/0107799 A1* | 5/2005 | Graf | A61F 2/4609 606/91 |
| 2005/0148843 A1* | 7/2005 | Roose | A61B 17/17 600/407 |
| 2005/0170311 A1 | 8/2005 | Tardieu et al. | |
| 2006/0094951 A1 | 5/2006 | Dean et al. | |
| 2006/0161167 A1* | 7/2006 | Myers | A61B 17/1746 606/91 |
| 2006/0184177 A1* | 8/2006 | Echeverri | A61B 17/1746 606/91 |
| 2006/0212044 A1 | 9/2006 | Bova et al. | |
| 2008/0161815 A1 | 7/2008 | Schoenefeld et al. | |
| 2008/0255584 A1* | 10/2008 | Beverland | A61B 5/103 606/130 |
| 2008/0287954 A1 | 11/2008 | Kunz et al. | |
| 2009/0163922 A1* | 6/2009 | Meridew et al. | 606/88 |
| 2009/0254093 A1 | 10/2009 | White et al. | |
| 2010/0016984 A1* | 1/2010 | Trabish | A61F 2/4609 623/22.32 |
| 2010/0076505 A1* | 3/2010 | Borja | A61F 2/4657 606/86 R |
| 2010/0082035 A1* | 4/2010 | Keefer | A61B 17/1746 606/91 |
| 2010/0087829 A1 | 4/2010 | Metzger et al. | |
| 2010/0137871 A1* | 6/2010 | Borja | A61F 2/4657 606/91 |
| 2010/0249657 A1* | 9/2010 | Nycz | A61F 2/4609 600/587 |
| 2010/0274253 A1* | 10/2010 | Ure | A61B 17/1746 606/91 |
| 2011/0092804 A1 | 4/2011 | Schoenefeld et al. | |
| 2011/0184419 A1 | 7/2011 | Meridew et al. | |
| 2011/0190775 A1* | 8/2011 | Ure | A61F 2/4609 606/91 |
| 2011/0224674 A1 | 9/2011 | White et al. | |
| 2012/0041445 A1* | 2/2012 | Roose | A61B 17/1746 606/96 |
| 2012/0109137 A1* | 5/2012 | Iannotti | A61B 17/1728 606/87 |
| 2012/0109138 A1 | 5/2012 | Meridew et al. | |
| 2012/0226283 A1 | 9/2012 | Meridew et al. | |
| 2013/0046310 A1* | 2/2013 | Ranawat | A61F 2/4609 606/91 |
| 2014/0052137 A1* | 2/2014 | Gibson | A61B 17/1746 606/91 |
| 2014/0107651 A1 | 4/2014 | Meridew et al. | |
| 2015/0112348 A1* | 4/2015 | Schoenefeld | A61B 17/1746 606/87 |

FOREIGN PATENT DOCUMENTS

| | | |
|---|---|---|
| WO | 9636284 A1 | 11/1996 |
| WO | 9926540 A1 | 6/1999 |
| WO | 9932045 A1 | 7/1999 |
| WO | 0177988 A2 | 10/2001 |
| WO | 2004017843 A1 | 3/2004 |
| WO | 2005110250 A1 | 11/2005 |
| WO | 2006060795 A1 | 6/2006 |
| WO | 2007097854 A2 | 8/2007 |
| WO | 2010124164 A1 | 10/2010 |

OTHER PUBLICATIONS

International Search Report of the International Searching Authority for PCT/CA2010/001828 filed Nov. 17, 2010.
Written Opinion of the International Searching Authority for PCT/CA2010/001828 filed Nov. 17, 2010.
International Preliminary Report on Patentability of the International Searching Authority for PCT/CA2010/001828 filed Nov. 17, 2010.
Hananouchi, T. et al., "Tailor-made surgical guide based on rapid prototyping technique for cup insertion in total hip arthroplasty", The International Journal of Medical Robotics and Computer Assisted Surgery, 5, 164-169 (2009).
Botha, Technical Report: "DeVIDE—The Delft Visualisation and Image Processing Development Environment" TU Delft, The Netherlands, May 30, 2005.
Rademacher et al., "Computer Assisted Orthopaedic Surgery by Means of Individual Templates Aspects and Analysis of Potential Application", MRCAS, 42-48 (1994).
Rademacher et al., "Computer Assisted Orthopaedic Surgery with Image Based Individual Templates", Clinical Orthopaedics and Related Research, 354, 28-38, (1998).
A pamphlet entitled "DePuy Preservation Design Rationale and Surgical Technique", DePuy Orthopaedics, Inc. 2006 (Rev. 3) 1-30.
Dechenne, C.L., et al., "A novel acetabular alignment guide for THR using selective anatomic landmarks on the pelvis", Journal of Biomechanics, 38, 1902-1908 (2005).
Echeverri, S., et al., "Reliable Acetabular Cup Orientation With a New Gravity-Assisted Guidance System", The Journal of Athroplasty, vol. 21, No. 3, 413-419 (2006).
Zheng, G., et al., "A novel patient-specific, gravity-assisted navigation system for acetabular cup placement", Session X: Total Hip Replacement—Part 2: New Devices, 145-148 (2009).
Hananouchi, T. et al., "Talior-made surgical guide reduces the learning curve for cup insertion", Session X: Total Hip Replacement—Part 2: New Devices, 152-154 (2009).

* cited by examiner

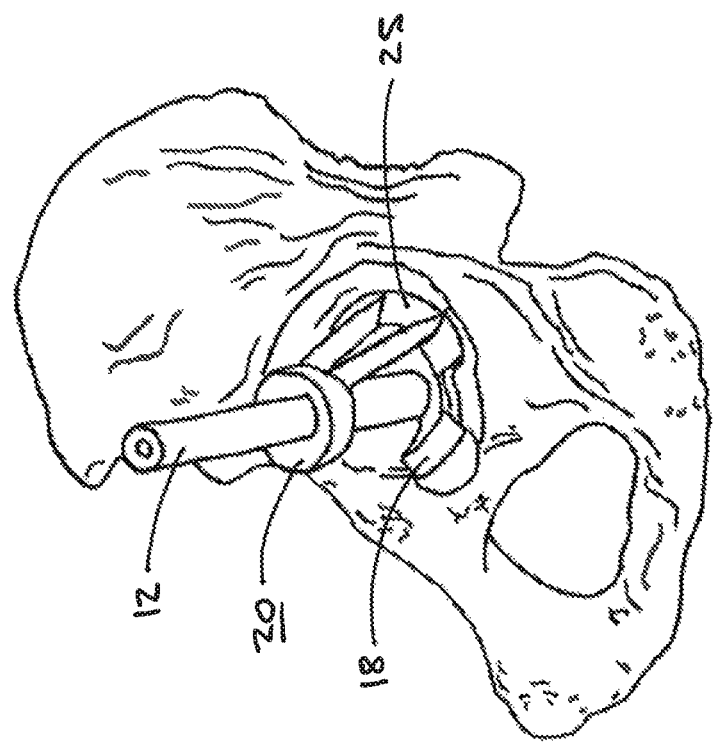

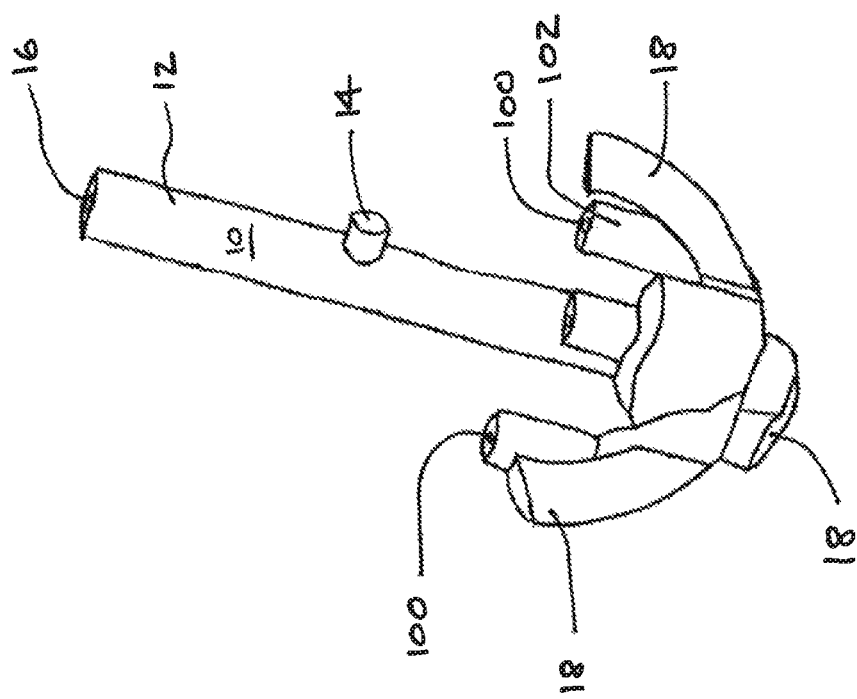

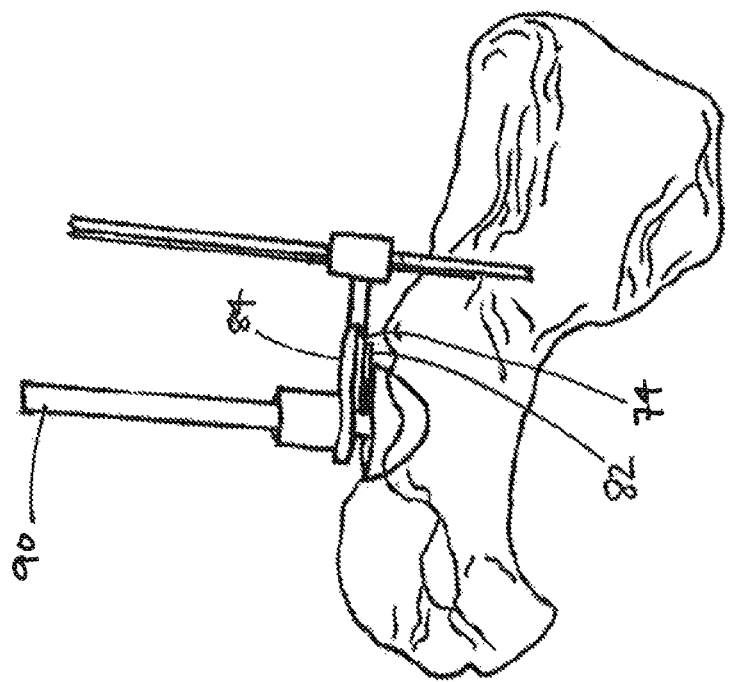
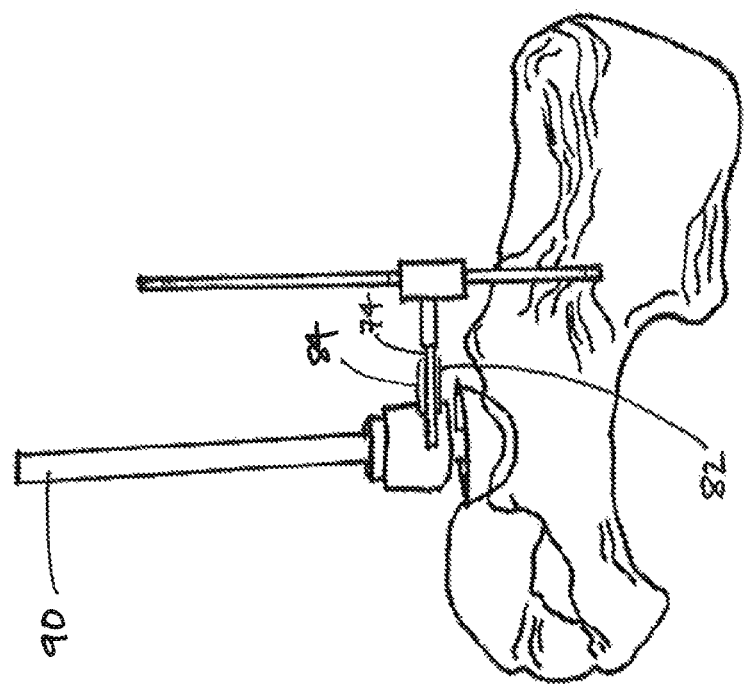
Figure 8b
Figure 8a

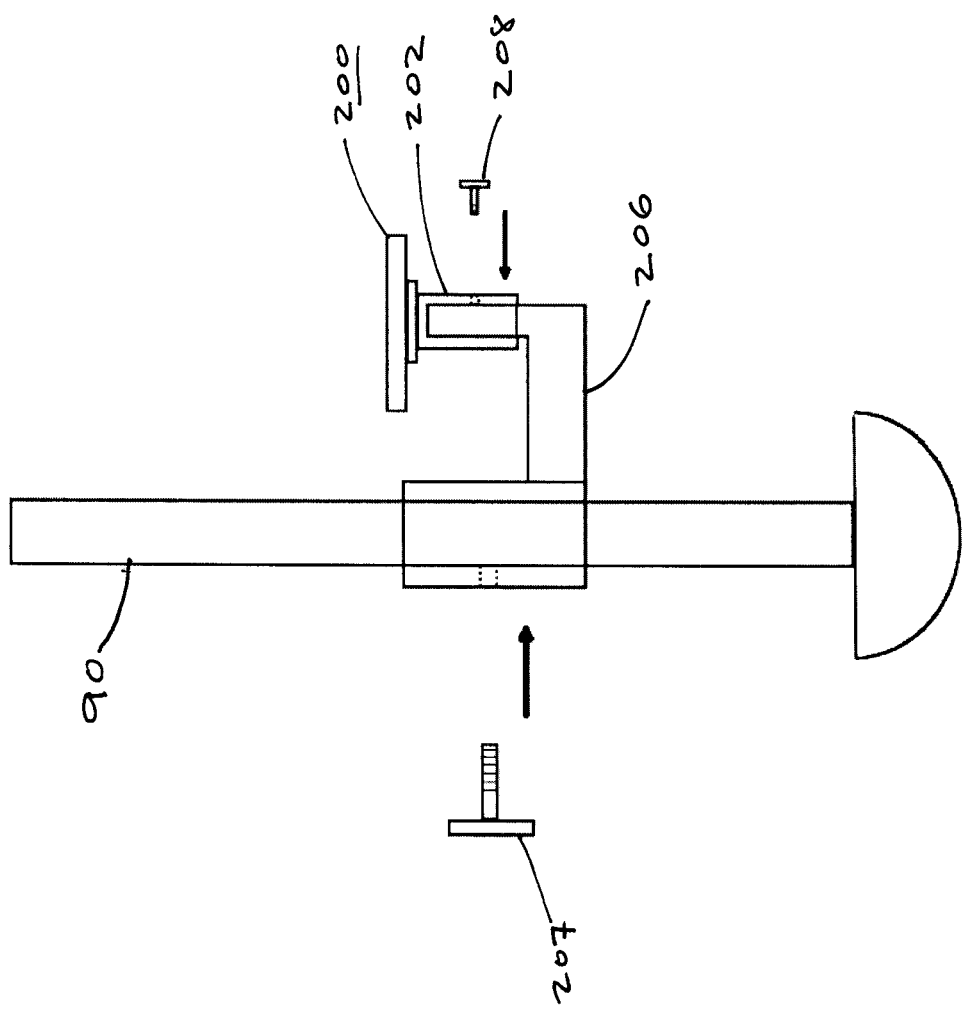

PATIENT-SPECIFIC GUIDE FOR ACETABULAR CUP PLACEMENT

RELATED APPLICATIONS

This is a 35 U.S.C. 371 national phase of International Application No. PCT/CA2010/001828, filed on 17 Nov. 2010, and claims the benefit of U.S. Provisional Application No. 61/262,073, filed on 17 Nov. 2009. The contents of both these applications are incorporated herein by reference in their entirety.

FIELD OF THE INVENTION

This invention relates to a device and method for placing a prosthetic cup of a ball and socket joint in a surgical procedure.

BACKGROUND OF THE INVENTION

Correct cup component placement during hip replacement or hip resurfacing procedures plays an important role for long-term success of the surgery. Non-optimal cup positioning can result in limited post-operative hip range of motion and can significantly increase the risk of dislocation of the femoral component.

Various image-guided and image-free computer-assisted systems have been proposed. All such systems are based on the installation of a tracking device in the operating room and attachment of sensors to the acetabulum and instruments. Furthermore, a computer-system is installed in the operating room, which displays the position of the instrument with respect to the planned cup position.

During such conventional procedures the surgeon orients the instruments to prepare the acetabulum and to impact the cup component into its final position by aligning them with accessible anatomical landmarks. During this procedure, the surgeon has visual access to only a very limited part of the anatomy, which does not represent the global alignment of the pelvis. This can result in misalignment of the cup component. Proposed computer-assisted solutions reduce this problem by planning the positioning of the cup component using pre- or intra-operative 3-D image modalities of the full pelvis. To transfer this planning into the patient's anatomy, registration between anatomy and planning is performed using locally accessible anatomical structures. On the other hand, to track the relative motion between anatomy and instruments, invasive fixation of the sensor to the anatomy and instruments, and the installation of expensive tracking technology in the operating theatre are necessary. The attached sensors are often prone to line-of-sight problems, which increase the complexity of the procedure. Furthermore, the registration procedure is often time consuming.

SUMMARY OF THE INVENTION

Described herein is a preoperatively designed guidance tool for intraoperative use during acetabular cup replacement surgery, comprising: a first guide mechanism that guides placement of a guide pin in the acetabulum; a second guide mechanism adapted to cooperate with the guide pin, that guides placement of one or more pins outside of the acetabulum; and a third guide mechanism adapted to cooperate with the one or more pins outside of the acetabulum, that guides at least one of reaming the acetabulum and placing an acetabular cup prosthesis.

The first guide mechanism may include a patient-specific template that registers with a selected surface of a patient's acetabulum. The first guide mechanism may include a verification tool adapted to cooperate with the patient specific template and having a mating surface that registers with a selected surface of the patient's anatomy.

Also described herein is a method for acetabular cup placement, comprising: placing a guide pin in the acetabulum according to preoperatively defined location and orientation; using the guide pin to locate a position and orientation of one or more pins outside of the acetabulum; using the one or more pins outside of the acetabulum to guide at least one of reaming the acetabulum and placing an acetabular cup prosthesis.

Placing the guide pin in the acetabulum may include using a patient-specific template that registers with a selected surface of a patient's acetabulum. Placing the guide pin in the acetabulum may include using a verification tool adapted to cooperate with the patient specific template and having a mating surface for registering with a selected surface of the patient's anatomy.

Also described herein is a preoperatively designed guidance tool for intraoperative use during acetabular cup replacement surgery, comprising: a patient-specific template having at least one surface that registers with a selected surface of the patient's acetabulum; and a guide portion that provides an orientation or a position and orientation of an acetabular cup according to a preoperatively planned orientation or position and orientation.

The guidance tool may further comprise a verification tool that cooperates with the guide portion and includes at least one mating surface that registers with a selected surface of the patient's anatomy, wherein correct positioning of the verification tool on the patient's anatomy confirms correct orientation of the patient-specific template in the patient's acetabulum.

The guidance tool may further comprise an external pin placing guide adapted to cooperate with the guide portion, that guides placement of one or more guide pins external to the acetabulum.

The guidance tool may further comprise an external pin placing guide adapted to cooperate with a central guide pin placed in the acetabulum, that guides placement of one or more guide pins outside of the acetabulum; wherein a position and/or orientation of the central guide pin in the acetabulum is set by the position and/or orientation of the guide portion in the acetabulum.

The guidance tool may further comprise an external pin placing guide adapted to cooperate with the central guide pin, that guides placement of one or more guide pins external to the acetabulum.

The guidance tool may further comprise means adapted to guide orientation of a surgical tool in the acetabulum according to orientation of the one or more guide pins external to the acetabulum. The means adapted to guide orientation of a surgical tool in the acetabulum may comprise a first portion that cooperates with the one or more guide pins external to the acetabulum; and a second portion that cooperates with the surgical tool; wherein the first portion and the second portion each include mating surfaces, such that mating of the mating surfaces of the first and second portions guides orientation of the surgical tool.

The guidance tool may further comprise a gravity sensing component adapted to cooperate independently with the guide portion and a surgical tool; wherein calibration of the gravity sensing component according to orientation of the guide portion guides orientation of the surgical tool when cooperating with the surgical tool.

The guidance tool may further comprise a gravity sensing component adapted to cooperate independently with the guide portion, one or more guide pins external to the acetabulum, and a surgical tool; wherein calibration of the gravity sensing component according to orientation of the guide portion and/or the one or more guide pins external to the acetabulum guides orientation of the surgical tool when cooperating with the surgical tool.

The guidance tool may further comprise a gravity sensing component adapted to cooperate independently with the guide portion, a central guide pin, one or more guide pins external to the acetabulum, and a surgical tool; wherein calibration of the gravity sensing component according to orientation of the guide portion, the central guide pin, and/or the one or more guide pins external to the acetabulum guides orientation of the surgical tool when cooperating with the surgical tool.

The gravity sensing component may be an electronic gravity sensing component or an analog gravity sensing component.

Also described herein is a method for transferring a preoperatively planned orientation or position and orientation of an acetabular cup to a patient during acetabulum cup replacement surgery, comprising: placing in the acetabulum a preoperatively designed guidance tool comprising: (i) a patient-specific template having at least one surface that registers with a selected surface of the patient's acetabulum; and (ii) a guide portion that provides the preoperatively planned orientation or position and orientation of the acetabular cup; and using the guide portion to orient a surgical tool to place the acetabular cup according to the preoperatively planned orientation or position and orientation.

Also described herein is a method of acetabulum cup replacement surgery, comprising: placing in the acetabulum a preoperatively designed guidance tool comprising: (i) a patient-specific template having at least one surface that registers with a selected surface of the patient's acetabulum; and (ii) a guide portion that provides a preoperatively planned orientation or position and orientation of the acetabular cup; and using the guide portion to orient a surgical tool to place the acetabular cup according to the preoperatively planned orientation or position and orientation.

The methods may further comprise verifying correct positioning of the patient-specific template on the patient's acetabulum prior to using the guide portion to orient a surgical tool.

The methods may further comprise using the guide portion to determine orientation of one or more guide pins external to the acetabulum.

The methods may further comprise using the guide portion to place a central guide pin in the acetabulum; wherein orientation of the central pin corresponds to orientation of the guide portion.

The methods may further comprise using the central guide pin to determine orientation of one or more guide pins external to the acetabulum.

The methods may further comprise using the one or more guide pins external to the acetabulum to guide orientation of a surgical tool in the acetabulum.

The methods may further comprise calibrating a gravity sensing component according to orientation of the guide portion or the central guide pin in the acetabulum; and using the calibrated gravity sensing component to guide orientation of a surgical tool.

The methods may further comprise calibrating a gravity sensing component according to orientation of the guide portion and/or the one or more guide pins external to the acetabulum; and using the calibrated gravity sensing component to guide orientation of a surgical tool.

The methods may comprise using an electronic gravity sensing component or an analog gravity sensing component.

BRIEF DESCRIPTION OF THE DRAWINGS

For a better understanding of the invention, and to show more clearly how it may be carried into effect, embodiments will be described, by way of example, with reference to the drawings, wherein:

FIG. 1d shows a template with a guide portion, and a verification tool of a patient-specific surgical tool positioned in an acetabulum, in accordance with another embodiment described herein.

FIG. 1e shows a template with a guide portion according to an embodiment.

FIGS. 8a and 8b show an alternative configuration of the arrangement of FIG. 7, including two alignment tabs fitted to the reamer, in accordance with an embodiment described herein.

FIG. 13 shows a surgical tool with a gravity sensing component fitted thereto, in accordance with an embodiment described herein.

DETAILED DESCRIPTION OF EMBODIMENTS

Figure 1B:
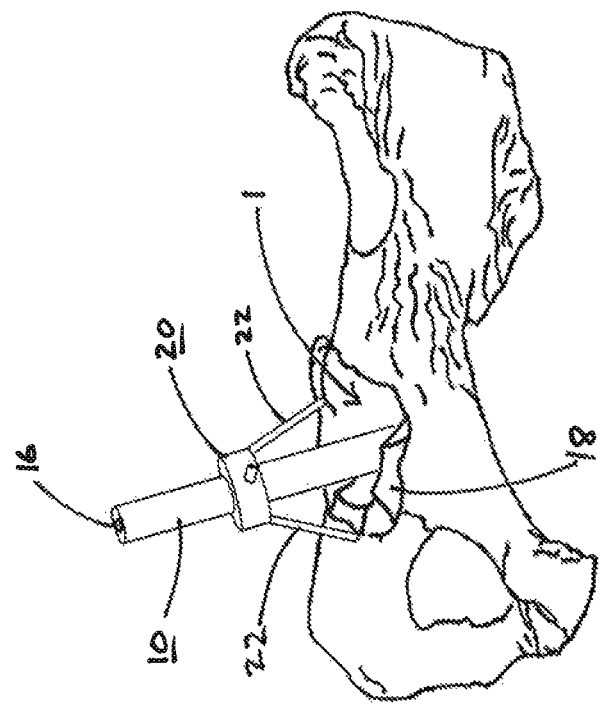
FIGS. 1a and 1b show a template with a guide portion, and a verification tool of a patient-specific surgical tool positioned in an acetabulum, in accordance with an embodiment described herein.

In one aspect, there is provided a patient-specific surgical tool for intraoperative use during acetabular cup replacement surgery, and a method therefor. The tool guides reaming of the acetabulum and impacting of the cup prosthesis into correct position, and provides accurate positioning of the cup prosthesis based on global alignment of the pelvis. Furthermore, the tool and method described herein requires little or no additional technical equipment in the operating theatre. The tool includes a patient-specific template component and a patient-specific verification component. The patient-specific template and verification components are preoperatively prepared based on imaging data of the patient's anatomy. The template component fits into the patient's acetabulum, registering with one or more anatomical landmarks, and includes a guide portion or mechanism for guiding a tool, such as a drill bit, and/or for placing a central guide pin in the acetabulum. The verification component registers with the template component and one or more preoperatively identified anatomical landmarks, thereby confirming accurate placement of the template component intra-operatively.

In particular, the patient-specific template component is designed having regard to one or more specific registration surfaces of the patient's anatomy, namely characteristic anatomical landmarks, bony structures and/or soft tissue (e.g., tendons, ligaments, etc.). For clarity, anatomical landmarks, bony structures and soft tissue are herein collectively termed "characteristic landmarks". One or more characteristic landmarks in the acetabulum are selected preoperatively and used in designing one or more respective mating surfaces of the template component, so as to uniquely register the template in a specific position/orientation in the acetabulum.

The guide portion may be integral with the template component and provides an indication of the desired position and orientation of the acetabular cup placement, as determined during the preoperative planning stage. For example, the guide portion may include a member with which other components may cooperate, so as to transfer the preoperatively planned cup orientation to the acetabulum. Such other components, which are not patient-specific, may include an external pin placing guide and/or a gravity sensing component (described in detail below), allow the surgeon to adjust the orientation of a cup impacting tool so as to install the cup in the acetabulum with the desired orientation, as determined during the preoperative planning stage.

The tool may also include other components that are not patient-specific, such as an external pin placing guide that cooperates with the central guide pin, for locating a position and orientation of one or more pins in a location of the bone outside of the acetabulum (i.e., external guide pins), and a component that cooperates with the one or more external guide pins, for guiding an instrument in the acetabulum such as a reamer or an acetabular cup impactor. Furthermore, the tool and method described herein allow the surgeon to modify the position of the reamer and/or impactor intraoperatively, if necessary. Thus, the tool and method described herein may be combined with conventional and semi-conventional techniques for reaming of the acetabulum and acetabular cup placement.

The template component may be prepared based on preoperatively obtained image data of the patient's pelvis. Image data may be obtained using, for example, computed tomography (CT). Other imaging technologies, and combinations thereof, may also be used. Accessible registration surfaces are identified in the dataset and the structural relationship between the planned cup position and such registration surfaces are saved. A registration surface may correspond to one or more distinct anatomical site, such as, for example, the acetabular fossa. The patient-specific template is created from mirror images of accessible registration surfaces selected from the saved accessible registration surfaces. The mirror images allow for unique positioning of the patient-specific template during the surgical intervention. The positioning of the patient-specific template may then be verified using the verification tool. The patient-specific template includes a guide portion for guiding a surgical cutting tool.

Figure 1A:
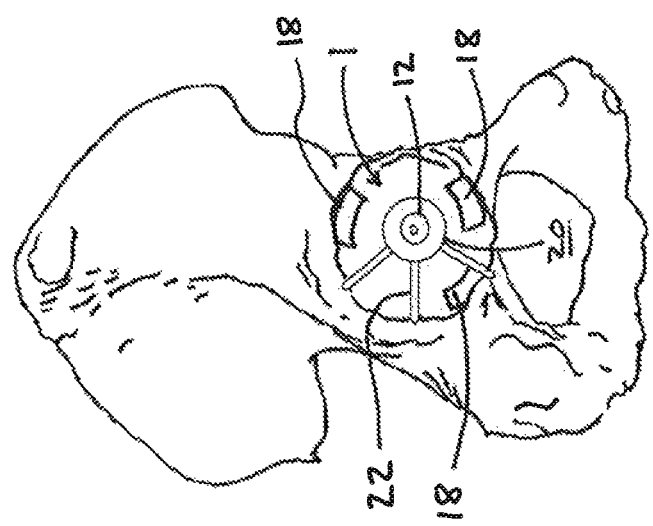
Figure 1C:
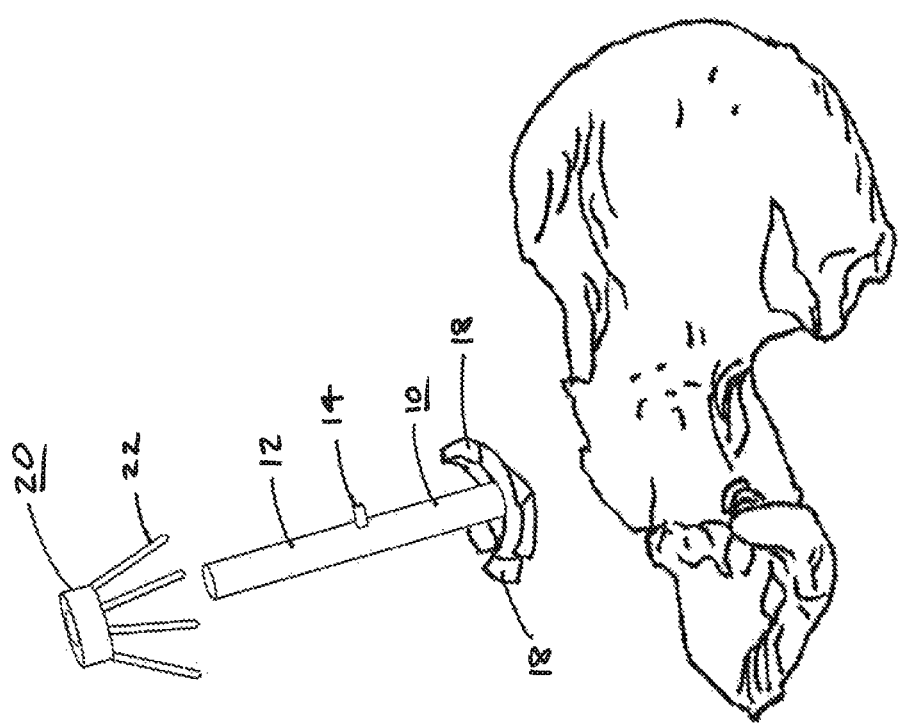
FIG. 1c is an exploded view of a template with a guide portion, and a verification tool according to an embodiment.
Figure 2:
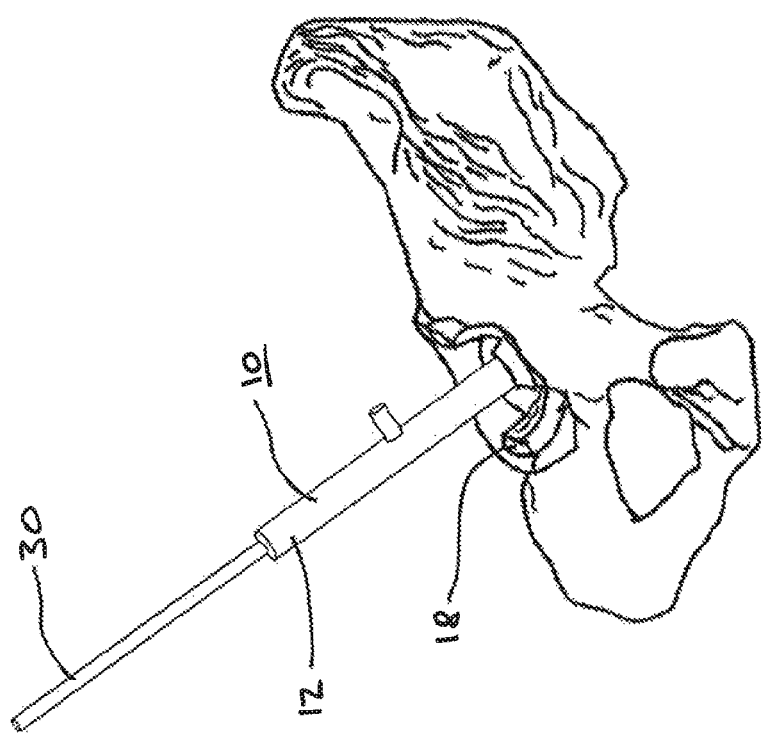
FIG. 2 shows a template and a guide portion with a central pin inserted into the guide portion, in accordance with an embodiment described herein.

In one embodiment, shown in the accompanying figures, the guide portion may be adapted for guiding a drill bit. FIGS. 1a and 1b show top and side views, respectively, of a patient-specific template 10 positioned in the acetabulum 1, with a verification tool 20 fitted to the template. The template 10 includes a key 14 (as can be seen in FIG. 2) adapted to register with a keyway in the verification tool 20, to ensure correct alignment of the verification tool 20 on the template 10. The template 10 includes portions 18 for uniquely registering with one or more anatomical landmarks within the acetabulum. The template 10 also includes a guide portion 12 with a hole 16 for a drill bit or a guide pin. The verification tool 20 has an opening or other suitable means to receive the shaft of the guide portion and cooperate therewith. The verification tool 20 includes one or more arms 22 (three are shown in the embodiment of FIGS. 1a and 1b) which uniquely register with one or more corresponding preoperatively identified landmarks on the patient's anatomy. Proper alignment of the arms 22 with respective preoperatively identified landmarks on the patient's anatomy confirms correct positioning of the template 10. FIG. 1c shows an exploded view of a template 10 with guide portion 12, and a verification tool 20 having four arms which uniquely register with one or more corresponding preoperatively identified landmarks on the patient's anatomy. FIG. 1d shows another embodiment of a verification tool, also referred to by reference numeral 20. This embodiment is also prepared preoperatively and includes a curved surface 25 that uniquely registers with a selected curved surface of the acetabulum.

When correctly placed in its unique position in the patient's acetabulum, the patient-specific template 10 allows the surgeon to drill a hole or place a central guide pin in a preoperatively determined location in the acetabulum. As shown in FIG. 2, a central guide pin 30 may be inserted through the hole 16 in the guide portion 12 of the template 10 and into the hole drilled in the patient's acetabulum. With the central guide pin 30 in place, the template may then be removed.

Figure 3:
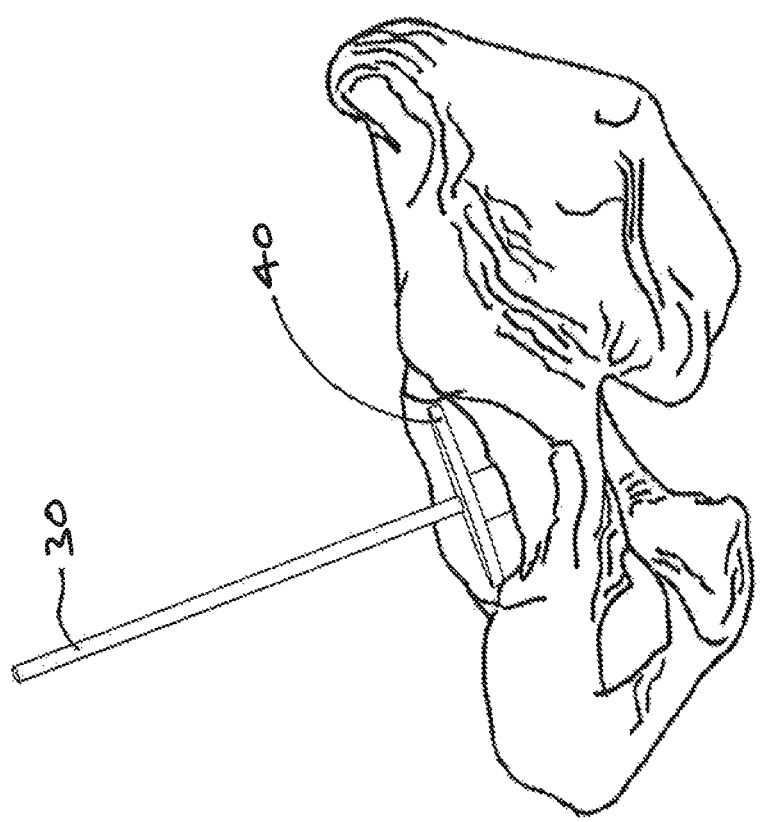
FIG. 3 shows a central pin placed in the acetabulum, with a plane template fitted to the central pin, in accordance with an embodiment described herein.

In FIG. 3, the central guide pin 30 is shown with an optional plane template 40 fitted thereto. The plane template 40 fits over the central guide pin 30 and is used to verify correct orientation of the prosthetic cup prior to placement. Plane templates may be available in different sizes, for different sizes of acetabulum, and allow the surgeon to visualize the final prosthetic cup orientation.

Figure 4B:
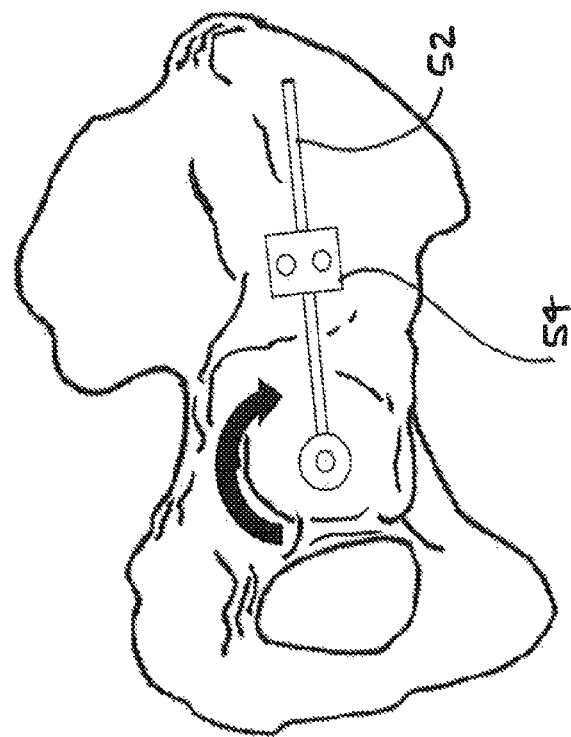
FIGS. 4a and 4b shows a central pin placed in the acetabulum, with a pin placing guide fitted to the central pin, in accordance with an embodiment described herein.
Figure 4A:
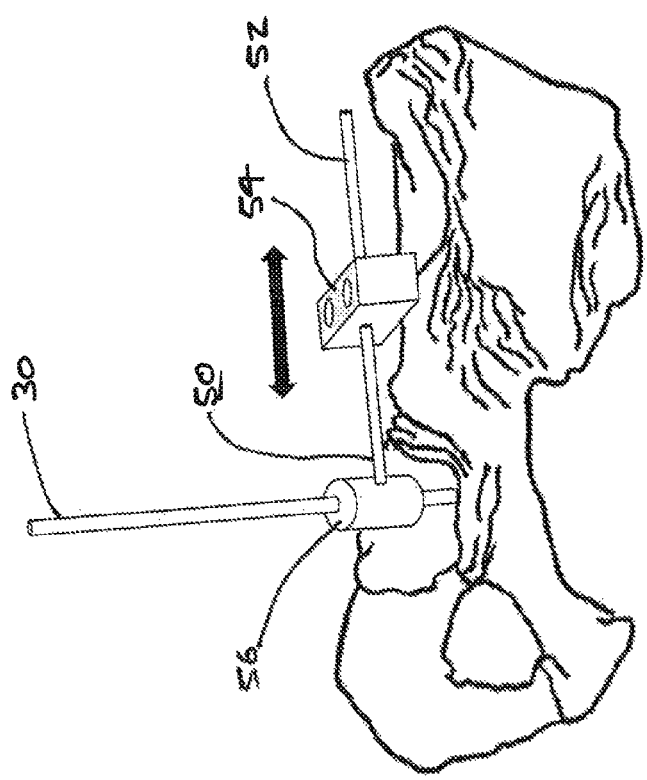

As shown in FIGS. 4a and b, after the plane template 40 is removed, an external pin placing guide 50 is fitted over the central guide pin 30. Alternatively, the external pin placing guide 50 may be made to fit over the guide portion 12 of the template 10, and thus used with or without placement of the central pin 30. In the embodiment shown, the external pin placing guide includes a collar 56 that cooperates with the central pin 30, an arm 52 and a slider 54. The slider has one or more guide holes for guiding placement of one or more external pins. The external pin placing guide 50 may be rotated around the central guide pin 30 and the slider 54 may be moved along the arm 52 to vary its distance from the guide pin 30, as shown by the arrows in FIGS. 4b and 4a, respectively. By rotating the pin placing guide and sliding the slider 54 along the arm 52, the surgeon may select a suitable location for inserting the one or more external pins in bone outside of the acetabulum. The selected location should be easy to access, free of extensive soft-tissue, and have good bone stock.

Figure 5:
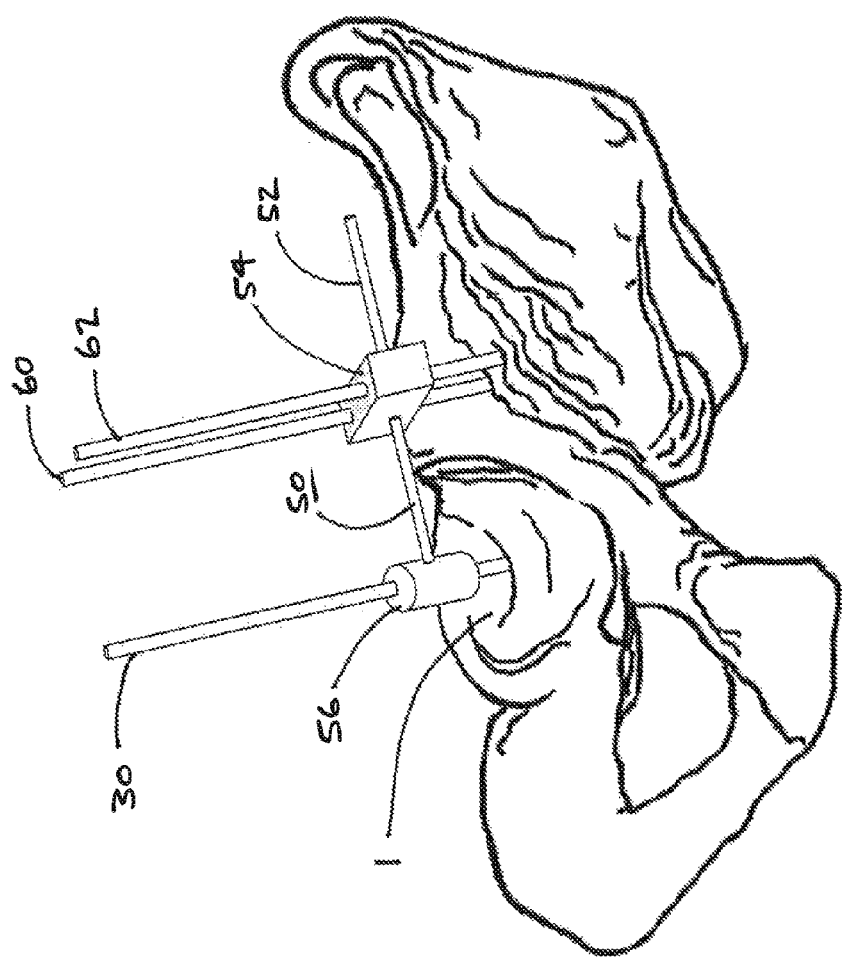
FIG. 5 shows a central pin placed in the acetabulum, with a pin placing guide and twin guide pins installed outside of the acetabulum, in accordance with an embodiment described herein.

In one embodiment, shown in FIG. 5, the slider 54 of the external pin placing guide 50 may include two holes for guiding placement of two pins 60,62. Such embodiment may be referred to herein as a twin pin pacing guide, and the two pins may be referred to as twin pins. In another embodiment, the collar 56 of the external pin placing guide 50 is adapted to cooperate with the shaft of the guide portion 12. According to this embodiment, the external pin placing guide may be used with the template component 10 and guide portion 12 in place in the acetabulum, without the need for placement of a central guide pin; that is, placement of the central guide pin is optional.

External pin placing guides may be provided with different off-set angles (e.g. 0.5°, 1°, 2°, etc.), which allows intra-operative modification of the eventual orientation of the prosthetic cup before the one or more external guide pins are placed. The offset may be implemented in the hole that accepts the central guide pin 30, or the hole or holes that accept the one or more external guide pins.

Figure 6:
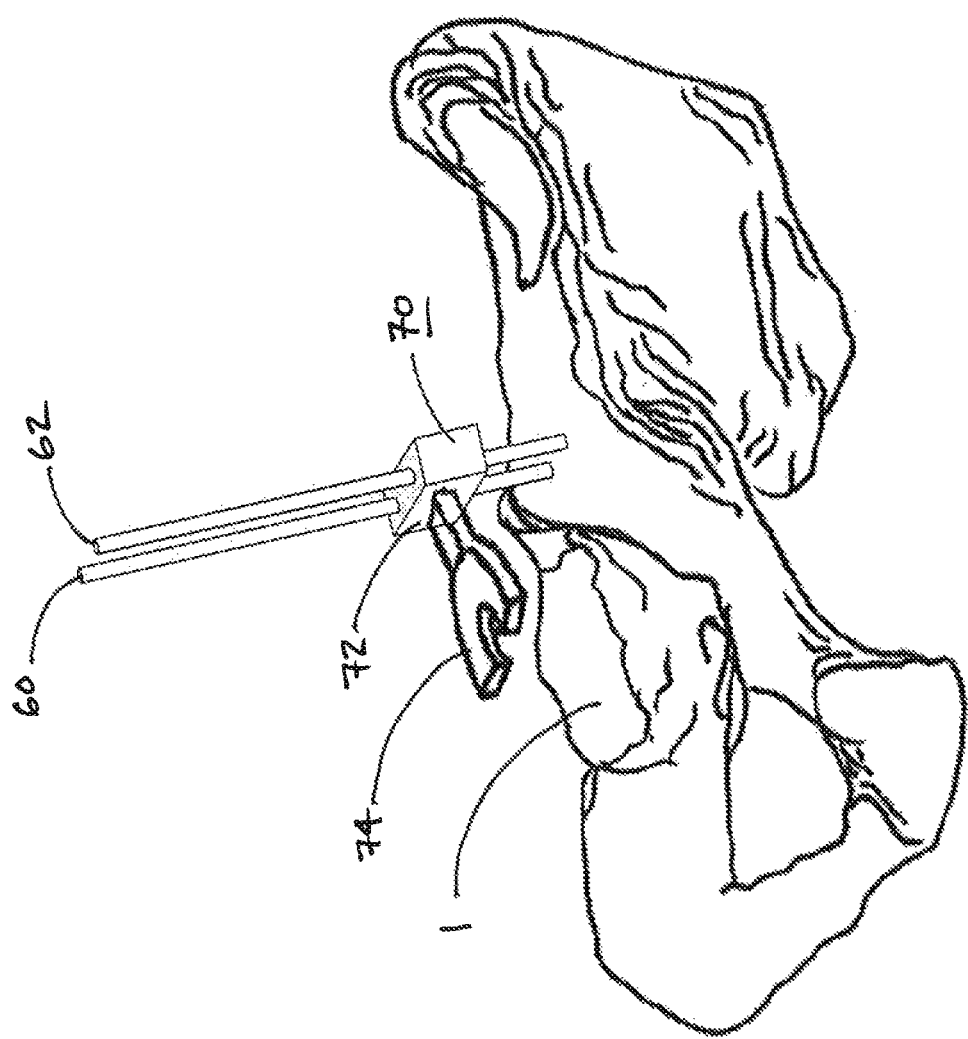
FIG. 6 shows an instrument guide plane fitted to twin pins installed outside of the acetabulum, in accordance with an embodiment described herein.
Figure 7:
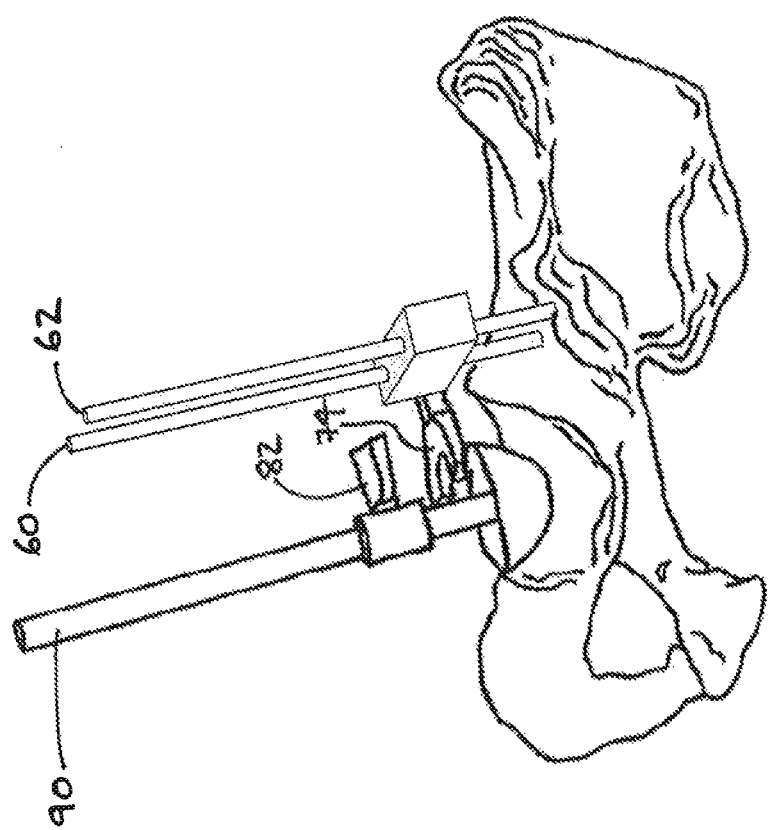
FIG. 7 shows the arrangement of FIG. 6 together with a reamer placed in the acetabulum, and an alignment tab fitted to the reamer that cooperates with the instrument guide plane, in accordance with an embodiment described herein.

As shown in FIG. 6, and with reference to the embodiment shown in FIG. 5, after the central guide pin 30 and twin pin placing guide 50 are removed, an instrument guide plane 70 is fitted to the twin pins 60,62. The instrument guide plane 70 has a base portion 72 with two substantially parallel holes for accepting the twin pins 60,62 with a sliding fit. A locking mechanism such as a screw or clamp may be provided with the base portion 72 to lock the instrument guide plane 70 in the correct position. The instrument guide plane 70 also includes an alignment portion 74 adapted to register with one or more corresponding alignment tabs fitted to a tool such as a reaming tool or an impactor, as shown in FIG. 7. For example, using one such alignment tab 82 allows the surgeon to manually orient the reamer or impactor with respect to the instrument guide plane. The use of two alignment tabs allows the surgeon to lock the orientation of the impactor with respect to the instrument guide plane.

For example, as shown in FIGS. 8a and 8b, upper 84 and lower 82 alignment tabs may be fitted to a tool 90 such as a reamer or an impactor. The lower alignment tab 82 is shown in FIG. 7. The upper and lower alignment tabs may each have a collar adapted for a sliding fit over the cylindrical handle portion of the reamer or impactor. Alternatively, the collar of the upper alignment tab may be adapted to fit over the collar of the lower alignment tab, as shown in FIGS. 8a and b. In use, the lower alignment tab 82 is aligned below the alignment portion 74, and the upper alignment tab is then slid over the alignment portion 74 and lower alignment tab 82, to lock the orientation of reamer or impactor, as shown in FIGS. 8a and 8b.

In some patients where the central guide pin 30 can be not placed in the acetabulum, the patient specific template can be left in the acetabulum and used to stabilize the guide pin during use of the twin pin placing guide 50 to place the twin pins.

The central guide pin 30 is positioned in the center of the hip (i.e., center of the acetabulum) To navigate reaming to the center of the acetabulum, a scale may be provided on the arm 52 of the external pin placing guide 50, and similarly on the instrument guide plane 70. The scales may be used to measure the distance from the one or more external guide pins to the center of the acetabulum, and then during reaming this distance can be reconstructed using the scale on the instrument guide plane.

If the surgeon decides not to use the above described method to navigate acetabular cup insertion, but to perform reaming of the acetabulum free-hand, the patient-specific template may include two, three, or more further guidance portions. The further guidance portions help the surgeon control reamer depth and centricity with respect to the center of the hip, and thereby achieve an optimal outcome during the free-hand reaming process. For example, as shown in FIG. 1e, the patient-specific template 10 may include three or more guide channels 100, which navigate the drilling of small diameter pilot holes of a prescribed depth into the intact acetabulum. For each pilot hole a drill guidance cylinder 102 may be integrated into the template, and height of the cylinder may be calibrated with a marked drill bit. The surgeon drills until the mark on the drill bit is lined up with the top edge of the guidance cylinder. In another embodiment the height/depth of the guide channels 100 themselves may be used to control the depth of the pilot holes. The depths of the drilled pilot holes correspond to the preoperatively planned reaming depth and are used to determine the correct amount of reaming.

Alternatively, the patient-specific template may include three or more guide channels to navigate the placement of three or more pins in the outer ring of the acetabulum. These pins may then be used to position a guidance tool for the reamer over the acetabulum. Such an embodiment of the guidance tool limits the movement of a conventional reamer around a pre-defined centre. Furthermore, a scale on the guidance tool may be used to navigate the depth of reaming.

In the embodiments described above, navigation and/or orientation of a tool such as a reamer or impactor in the acetabulum may be carried out using distal guide pins, the alignment portion 74, and one or more alignment tabs 82,84 associated with the tool. The embodiments described below, with reference to FIGS. 9 to 13, provide alternative methods and apparatus to verify navigation and/or orientation of a tool such as a reamer or impactor.

Figure 9:
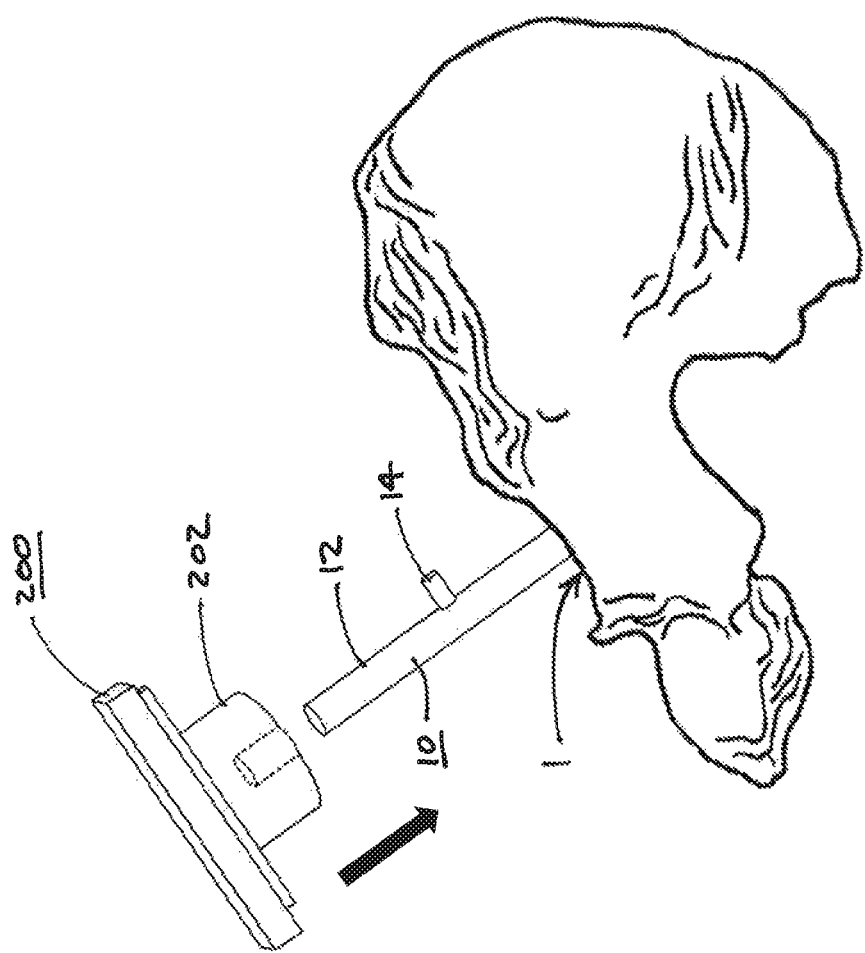
FIG. 9 shows a template and guide portion of a patient-specific surgical tool, in place in an acetabulum, and a gravity sensing component, in accordance with an embodiment described herein.

Referring to FIG. 9, a patient-specific template 10 with guide portion 12 is shown positioned in the acetabulum. As previously described, the surgeon registers the template 10 to the acetabulum by adjusting one or more mirror image surfaces of the template to one or more corresponding acetabulum surfaces. Such surfaces are not visible in FIG. 9.

Also shown in FIG. 9 is a gravity sensing component 200, which has a collar 202 adapted to receive the shaft of guide portion 12. An adapter 204, such as that shown in FIG. 12, used with the collar 202 may allow the gravity sensing component to be mounted on a guide pin, such as the central guide pin 30 or an external guide pin as described with respect to the previous embodiments.

Figure 10:
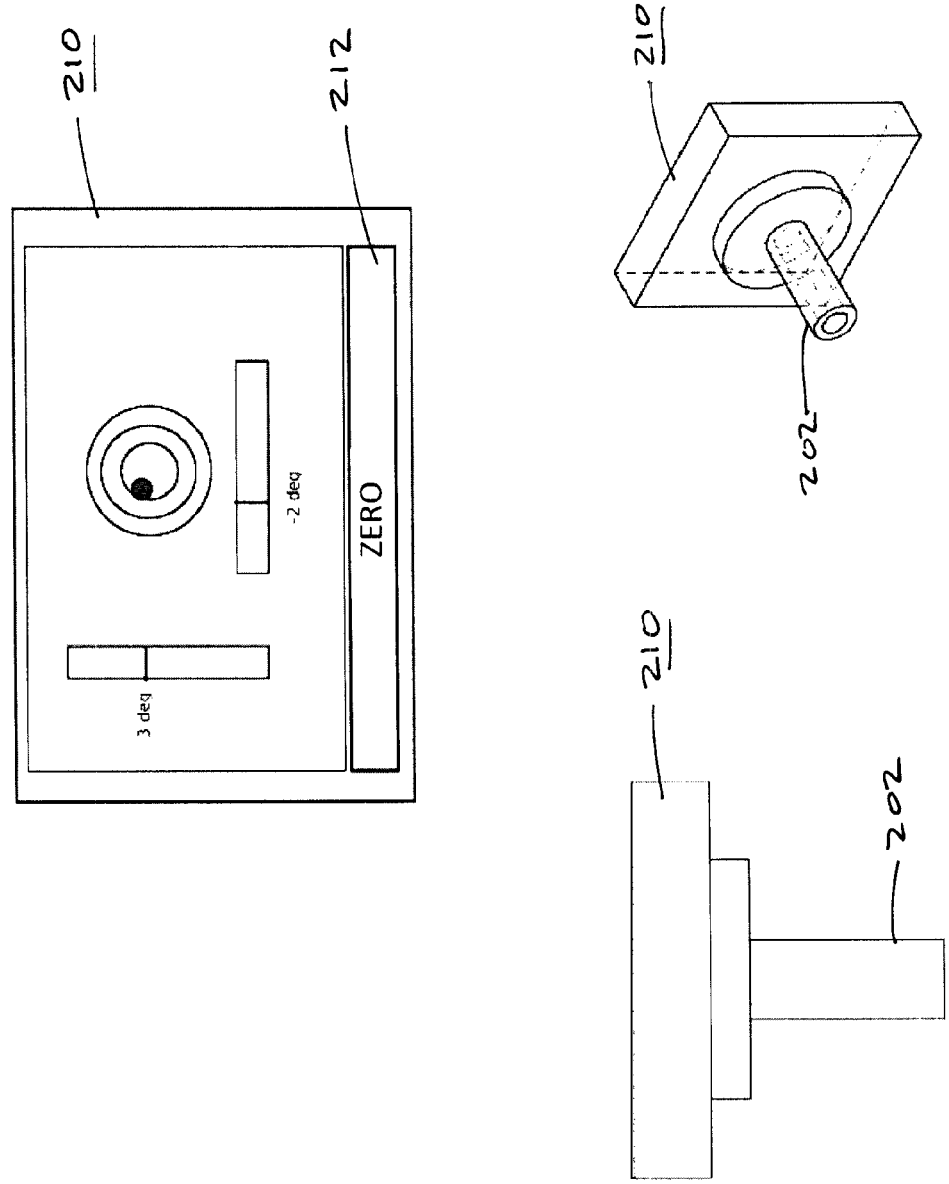
FIG. 10 shows an electronic gravity sensing component in accordance with an embodiment described herein.

In one embodiment, shown in FIG. 10, the gravity sensing component is an electronic gravity sensing component 210 which can measure deviation from the axis of gravity in two directions. For example, in one implementation the electronic gravity sensing component 210 may include two accelerometers, mounted in a 90 degree orientation to each other. Other implementations will be apparent to those of ordinary skill in the art. The electronic gravity sensing component may have a "zeroing" function 212, which, when activated by a push-button or other convenient means, calibrates the electronic gravity sensing component by saving a current orientation as a reference orientation.

In use, the electronic gravity sensing component 210 is mounted on the shaft of the guide portion 12, which is correctly oriented in the acetabulum, or to a correctly oriented guide pin (e.g., central pin or external guide pin) using a suitable adaptor. For example, such mounting may dispose the electronic gravity sensing component 210 orthogonal to the guide portion 12 or guide pin. Correct orientation of the guide portion 12 and guide pin may first be determined using one or more of the verification tools and procedures described above. Upon activating the zeroing function, the orientation of the electronic gravity sensing component 210 as mounted to the guide portion 12 or guide pin is registered as the reference orientation. That is, the electronic gravity sensing component is then calibrated for the correct orientation. The electronic gravity sensing component 210 may then be removed from the guide portion or guide pin.

Figure 11:
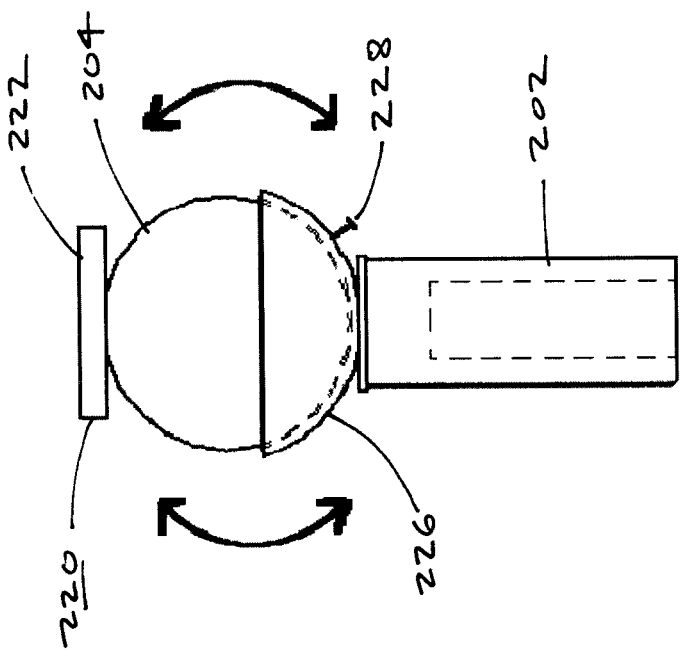
FIG. 11 shows an analog gravity sensing component in accordance with an embodiment described herein.
Figure 11:
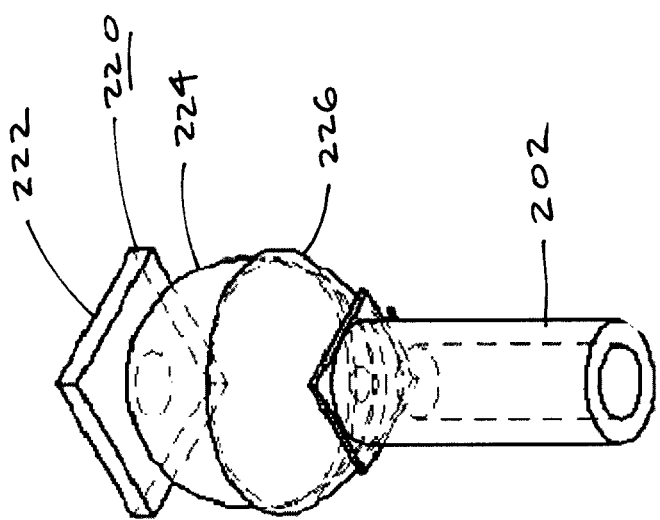

In an alternative embodiment, the gravity sensing component may be an analog gravity sensing component 220. For example, as shown in FIG. 11, the analog gravity sensing component 220 may comprise a bubble level 222. The bubble level may be moveably attached to the collar 202 using, for example, a ball 224 and socket 226 mechanism. The ball and socket mechanism allows the bubble level 222 to be "zeroed" in a selected orientation when the analog gravity sensing component 220 is mounted to the shaft of the guide portion 12 or a guide pin. The ball and socket mechanism may be locked in the zeroed position using a suitable mechanical lock 228 such as a clamp or set-screw, which when locked calibrates the analog gravity sensing component by preventing relative movement between the ball and socket.

In use, the analog gravity sensing component 220 is mounted on the shaft of the guide portion 12, which is correctly oriented in the acetabulum, or to a correctly oriented guide pin (e.g., central guide pin or external guide pin) using a suitable adaptor. For example, such mounting may dispose the analog gravity sensing component 220 orthogonal to the guide portion 12 or guide pin. Correct orientation of the guide portion 12 and guide pin may be determined using one or more of the verification tools and procedures described above. The bubble level is then zeroed using the ball and socket mechanism, and locked in the zeroed position using the mechanical lock 228. Thus, the orientation of the analog gravity sensing component 220 as mounted to the guide portion 12 or guide pin is saved as the reference orientation. That is, the analog gravity sensing component is then calibrated for the correct orientation. The analog gravity sensing component 220 may then be removed from the guide portion or guide pin.

It is noted that the electronic gravity sensing component 210 and the analog gravity sensing component 220 may be used with the guide portion 12, without using an optional guide pin such as the central guide pin 30 or an external guide pin. However, insofar as the central guide pin 30 may stabilize the orientation of the template 10 in the acetabulum, it may be desirable to install the central guide pin 30. It may also be desirable to install the central pin 30 as it permits use of a plane template 40, which allows the surgeon to visualize the orientation of the prosthetic cup, as previously described. Use of an external guide pin may be desirable because it permits the surgeon to verify correct orientation any time during the surgery; for example, to correct for possible movement of the patient's anatomy during the surgery.

Figure 12:
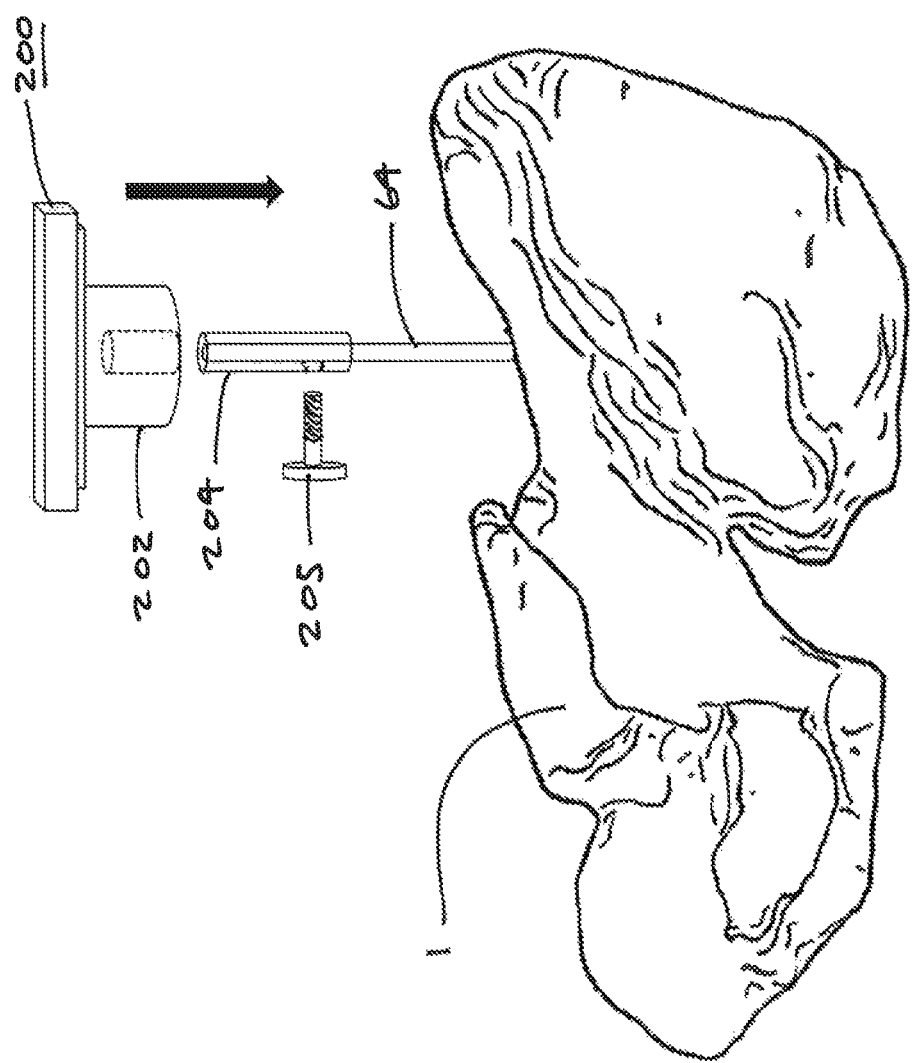
FIG. 12 shows a distal guide pin and gravity sensing component for use therewith, in accordance with an embodiment described herein.

Use of an external guide pin also permits verification of the gravity sensing component calibration to be carried out. As shown in FIG. 12, the analog or electronic gravity sensing component, referred to generally by reference numeral 200, may be placed over an external guide pin 64, using an adapter 204 as may be required, with optional set screw 205. The acetabulum is shown at 1. Calibration of the gravity sensing device may then be verified and repeated if necessary, as described above. This procedure may be repeated at any time during the surgery, for example, to correct for possible movement of the patient's anatomy.

As shown in FIG. 13, the calibrated analog or electronic gravity sensing component, referred to generally by reference numeral 200, may then be placed on a tool such as an impactor, using a suitable adapter 206, if necessary, with optional fasteners such as set screws 207,208. The embodiment shown in FIG. 13 holds the gravity sensing component in alignment with the tool while allowing the surgeon to grip the tool. In this manner an axis of the gravity sensing component may be aligned with an axis of the tool, such that the correct orientation of the gravity sensing component may be transferred to the tool. The surgeon may then modify the tool orientation until the gravity sensing component shows alignment with the tool, and hence correct orientation of the tool.

Although embodiments have been described herein primarily in respect of the acetabulum, it will be appreciated by those of ordinary skill in the art that such apparatus and methods may be used in similar surgical procedures in other ball and sockets joints, such as, for example, the shoulder.

Embodiments of the invention are further described by way of the following non-limiting examples.

EXAMPLE 1

Method for Acetabular Cup Placement According to a First Embodiment

A patient-specific template 10 with guide portion 12 is positioned in the acetabulum of a patient and oriented correctly according to the unique fit provided by the mating surfaces 18 of the template and respective landmarks on the patient's anatomy. Correct orientation of the template 10 and guide portion 12 is verified using a verification tool that cooperates with the guide portion 12. An electronic gravity sensing component 210 or analog gravity sensing component 220 (referred to hereinafter as a gravity sensing component 200) is fitted to the guide portion 12 and calibrated according to the orientation of the guide portion 12. The template 10 and guide portion 12 is removed from the acetabulum and the acetabulum is reamed to the correct size for the prosthetic acetabular cup to be inserted. The prosthetic acetabular cup is engaged with an impacting tool, to which the gravity sensing component 200 has been fitted, and placed in the acetabulum. The impacting tool is adjusted to the correct orientation as determined from the calibrated gravity sensing component 200, and then used to drive the acetabular cup into the acetabulum at the correct orientation.

EXAMPLE 2

Method for Acetabular Cup Placement According to a Second Embodiment

A patient-specific template 10 with guide portion 12 is positioned in the acetabulum of a patient and oriented correctly according to the unique fit provided by the mating surfaces 18 of the template and respective landmarks on the patient's anatomy. Correct orientation of the template 10 and guide portion 12 is verified using a verification tool that cooperates with the guide portion 12. An electronic gravity sensing component or analog gravity sensing component (referred to hereinafter as a gravity sensing component 200) is fitted to the guide portion 12 and calibrated according to the orientation of the guide portion 12. The gravity sensor is removed and an external pin placing guide 50 is fitted to the guide portion 12 and used to place an external guide pin in a suitable location of the pelvis. Correct orientation of the external guide pin is verified by fitting the gravity sensing component 200 thereto, wherein the orientation of the external guide pin is correct when it is the same as the orientation of the template 10 and guide portion 12. The template 10 and guide portion 12 and external pin placing guide 50 are removed from the acetabulum and the acetabulum is reamed to the correct size for the prosthetic acetabular cup to be inserted. The prosthetic acetabular cup is engaged with the impacting tool and the prosthetic acetabular cup is placed in the acetabulum. Correct orientation of the patient's anatomy is confirmed by checking orientation of the external guide pin. If the external guide pin is no longer correctly oriented, the patient's position has shifted. In such case the gravity sensing component 200 is newly calibrated using the external guide pin. Upon confirming and/or establishing correct calibration, the gravity sensing component 200 is fitted to the impacting tool. The impacting tool is adjusted to the correct orientation as determined from the calibrated gravity sensing component 200, and then used to drive the acetabular cup into the acetabulum at the correct orientation.

EXAMPLE 3

Method for Acetabular Cup Placement According to a Third Embodiment

A patient-specific template 10 with guide portion 12 is positioned in the acetabulum of a patient and oriented correctly according to the unique fit provided by the mating surfaces 18 of the template and respective landmarks on the patient's anatomy. Correct orientation of the template 10 and guide portion 12 is verified using a verification tool that cooperates with the guide portion 12. An external pin placing guide 50 is fitted to the guide portion 12 and used to place a pair of external guide pins 60,62 in a suitable location of the pelvis. The template 10 and guide portion 12 and external pin placing guide 50 are removed from the acetabulum and the acetabulum is reamed to the correct size for the prosthetic acetabular cup to be inserted. An instrument guide plane 70 is fitted to the guide pins 60,62. One or more alignment tabs are fitted to an impacting tool. The prosthetic acetabular cup is placed in the acetabulum. The impacting tool engages the prosthetic acetabular cup and is adjusted to correct orientation by aligning the alignment tabs with the instrument guide plane. The impacting tool is then used to drive the acetabular cup into the acetabulum at the correct orientation.

EXAMPLE 4

Method for Acetabular Cup Placement According to a Fourth Embodiment

A patient-specific template 10 with guide portion 12 is positioned in the acetabulum of a patient and oriented correctly according to the unique fit provided by the mating surfaces 18 of the template and respective landmarks on the patient's anatomy. Correct orientation of the template 10 and guide portion 12 is verified using a verification tool that cooperates with the guide portion 12. A drill bit is inserted into the hole 16 of the guide portion 12 and used to drill a hole in the acetabulum. A central guide pin 30 is inserted into the hole 16 in the guide portion 12 and into the acetabulum. The template 10 with guide portion 12 is removed from the acetabulum. An external pin placing guide 50 is fitted to the central guide pin 30 and used to place a pair of external guide pins 60,62 in a suitable location of the pelvis. The central pin 30 and external pin placing guide 50 are removed from the acetabulum and the acetabulum is reamed to the correct size for the prosthetic acetabular cup to be inserted. An instrument guide plane 70 is fitted to the guide pins 60,62. One or more alignment tabs are fitted to an impacting tool. The prosthetic acetabular cup is placed in the acetabulum. The impacting tool engages the prosthetic acetabular cup and is adjusted to correct orientation by aligning the alignment tabs with the instrument guide plane. The impacting tool is then used to drive the acetabular cup into the acetabulum at the correct orientation.

EQUIVALENTS

Those of ordinary skill in the art will recognize, or be able to ascertain through routine experimentation, equivalents to the embodiments described herein. Such equivalents are within the scope of the invention and are covered by the appended claims.

The invention claimed is:

1. A preoperatively designed guidance tool for intraoperative use during acetabular cup replacement surgery, comprising:
    a patient-specific template having at least one surface that is adapted to uniquely register with a selected corresponding inside surface of the patient's acetabulum;
    a removable verification tool; and
    a guide portion that guides the verification tool and at least one of a gravity sensing component and a surgical tool;
    wherein the verification tool includes at least one member that is adapted to contact an anatomical landmark of the patient's anatomy, wherein contact of the verification tool with the anatomical landmark confirms correct orientation of the patient-specific template in the patient's acetabulum.

2. The guidance tool of claim 1, wherein the surgical tool comprises an external pin placing guide that cooperates with the guide portion and is adapted to guide placement of one or more external pins outside of the acetabulum.

3. The guidance tool of claim 2, further comprising a guide component that cooperates with the one or more external pins and is adapted to guide orientation of a second surgical tool in the acetabulum according to orientation of the one or more external pins.

4. The guidance tool of claim 3, wherein the guide component comprises:
    a first portion that cooperates with the one or more external pins; and a second portion;
wherein an alignment of the second portion with the surgical tool guides orientation of the surgical tool.

5. The guidance tool of claim 1, wherein the surgical tool comprises a guide pin that cooperates with the guide portion; and
wherein an external pin placing guide cooperates with the guide pin and is adapted to guide placement of one or more external pins outside of the acetabulum;
wherein at least one of a position and orientation of the guide pin is set by at least one of the position and orientation of the guide portion of the guidance tool.

6. The guidance tool of claim 1, wherein the surgical tool comprises a guide pin, wherein the guide portion is adapted to guide placement of the guide pin in the acetabulum;
wherein the gravity sensing component is adapted to cooperate independently with the guide pin and a second surgical tool;
wherein calibration of the gravity sensing component according to orientation of the guide pin guides orientation of the second surgical tool when the gravity sensing component is cooperating with the second surgical tool.

7. The guidance tool of claim 1, wherein the gravity sensing component is an electronic gravity sensing component, an analog gravity sensing component, or a combination thereof.

8. A method for intraoperatively using a preoperatively designed guidance tool during acetabulum cup replacement surgery, comprising:
placing in the acetabulum the preoperatively designed guidance tool comprising:
(i) a patient-specific template having at least one surface that uniquely registers with a selected inside surface of the patient's acetabulum; and
(ii) a guide portion that guides a removable verification tool and at least one of a gravity sensing component and a surgical tool, wherein the removable verification tool is adapted to contact an anatomical landmark of the patient's anatomy;
verifying correct positioning of the patient-specific template in the patient's acetabulum using the removable verification tool, wherein contact of the removable verification tool with the anatomical landmark confirms correct positioning of the patient-specific template in the patient's acetabulum;
calibrating the gravity sensing component according to the guide portion when the patient-specific template is registered in the patient's acetabulum; and
using the calibrated gravity sensing component to guide the surgical tool.

9. The method claim 8, wherein the surgical tool comprises an external pin placing guide, the method further comprising:
using the guide portion and the external pin placing guide to determine at least one of position and orientation of one or more external pins outside of the acetabulum; and
using the one or more external pins outside of the acetabulum to determine at least one of position and orientation of the surgical tool in the acetabulum.

10. The method of claim 8, wherein the surgical tool comprises a guide pin, the method further comprising:
using the guide portion to place the guide pin in the acetabulum;
using the guide pin to determine at least one of position and orientation of one or more external pins outside of the acetabulum; and
using the external pins outside of the acetabulum to determine at least one of position and orientation of the surgical tool in the acetabulum.

11. The method of claim 8, further comprising:
using the calibrated gravity sensing component to guide orientation of the surgical tool in the acetabulum;
wherein the surgical tool is used to place the acetabular cup in the acetabulum according to a preoperatively planned orientation or position and orientation.

12. The method of claim 8, wherein the surgical tool comprises a guide pin, the method further comprising:
using the guide portion to place the guide pin in the acetabulum;
calibrating the gravity sensing component according to orientation of the guide pin in the acetabulum; and
using the calibrated gravity sensing component to guide orientation of a second surgical tool in the acetabulum.

13. The method of claim 8, wherein the gravity sensing component is an electronic gravity sensing component, an analog gravity component, or a combination thereof.

* * * * *